United States Patent [19]

Shaw et al.

[11] Patent Number: 5,085,832

[45] Date of Patent: Feb. 4, 1992

[54] DISPENSING MECHANISM

[75] Inventors: James D. Shaw, Hilton; Nicholas Want, Rochester, both of N.Y.

[73] Assignee: Eastman Kodak Company, Rochester, N.Y.

[21] Appl. No.: 726,138

[22] Filed: Jul. 5, 1991

Related U.S. Application Data

[63] Continuation-in-part of Ser. No. 556,692, Jul. 20, 1990, abandoned.

[51] Int. Cl.$^5$ ............................................. G01N 35/00
[52] U.S. Cl. .................................... 422/63; 422/64; 422/67; 422/100
[58] Field of Search ...................... 73/53; 74/816, 817; 422/63, 64, 67, 100; 436/46

[56] References Cited

U.S. PATENT DOCUMENTS

| | | | |
|---|---|---|---|
| 3,188,181 | 6/1965 | Peterson et al. | 422/100 |
| 3,592,605 | 12/1969 | Masayoshi | 422/64 |
| 3,948,605 | 4/1976 | Atwood et al. | 422/63 |
| 4,046,511 | 9/1977 | Stabile | 422/64 |
| 4,050,355 | 9/1977 | Niskanen | 74/817 |
| 4,347,750 | 9/1982 | Tersteeg et al. | 422/64 |
| 4,452,899 | 6/1984 | Alston | 422/63 |
| 4,656,007 | 4/1987 | Douchy et al. | 422/63 |

OTHER PUBLICATIONS

Eastman Kodak User Manual Publication No. XP3080-13, pp. 5, 6 and 12 (1986).

Primary Examiner—Michael S. Huppert
Assistant Examiner—Kenneth Bomberg
Attorney, Agent, or Firm—Dana M. Schmidt

[57] ABSTRACT

A liquid dispensing mechanism is described for moving a dispensing tip from an aspirating station to a dispensing station, preferably through a circle of rotation. To move the tip first vertically, then rotationally, and then vertically, the mechanism mounts the tip and a pump on a carrier that frictionally engages a cam over which the carrier is mounted. The pump is slidably mounted for reciprocation on the carrier, and has a cam follower that extends through a slot in the carrier to the cam inside. Apparatus is provided for limiting the rotation of the carier between two circumferential positions to force the cam follower, and hence the pump and tip, to move relative to the still-rotating cam.

9 Claims, 8 Drawing Sheets

DISPENSING MECHANISM

This is a continuation-in-part of application Ser. No. 556,692, filed July 20, 1990 now abandoned.

FIELD OF THE INVENTION

The invention relates to a liquid dispensing device useful in an analyzer, of the type that repeatedly aspirates from the same source.

BACKGROUND OF THE INVENTION

Liquid dispensing mechanisms are used in clinical analyzers to aspirate and dispense various liquids as needed. In the "Ektachem 400"® and/or "Ektachem 700"® analyzers manufactured by Eastman Kodak Company, in addition to aspirating and dispensing sample, a reference liquid has to be aspirated and dispensed when a potentiometric analysis is conducted using ISE test elements. The mechanism that handles the reference liquid is somewhat complex, for several reasons. First, the pump and the removable tip mounted thereon has to move between two operative, "down" positions that correspond to the aspirating position at a reservoir and the dispense position at a dispensing station. Between these positions, it moves to a raised inoperative position. Conveniently, movement between "down" positions is done rotationally wherein the two operative positions are circumferentially positioned on a circle of motion. Second, complexity is introduced because the tip insertion occurs at an angle from the vertical, for clearance purposes. Hence, it is not sufficient to simply raise the pump and its tip, but rather, to raise it along a diagonal.

The mechanism to achieve this on the aforesaid analyzers available from Eastman Kodak Company has been useful and generally satisfactory. However, it has required the use of a large number of complex parts, including a barrel cam, a cam follower mounted to always ride on the cam, the cam follower being connected to a yoke hingedly and rotationally connected to a rack cylinder that drives a pinion gear, a second rack mounted in the pump that is in turn driven by the pinion gear, and a modified Geneva mechanism for controlling the rotation of the barrel cam. Portions of this device can be seen in the Eastman Kodak User Manual entitled "E700/E500 Service Manual", Pub. #XP3080-13, p. 5, 6 & 12, dated 8/86. Because so many moving parts are required, this conventional dispensing mechanism has been more expensive to build, or maintain, than it would be if it used fewer moving parts.

Therefore, prior to this invention, there has been a need for a simpler liquid-aspirating and dispensing mechanism requiring fewer moving parts.

SUMMARY OF THE INVENTION

We have constructed a liquid dispensing mechanism that solves the above-mentioned needs.

More particularly, in accord with one aspect of the invention, there is provided a liquid dispensing mechanism for use in an analyzer and comprising a pump, a tip support on the pump for holding a liquid-containing tip, means for moving the pump and a tip on the support vertically and rotationally between at least two operative positions in which liquid is either aspirated into a tip or dispensed from a tip, and inoperative positions above and between the operative positions, the moving means including a rotatable three-dimensional cam, a cam follower mounted to move on the cam, and means for rotating the cam about a vertical axis between the at least two operative positions in response to command signals. The mechanism is improved in that the moving means further includes a carrier mounted over and surrounding the cam, the pump being slidably mounted for reciprocation on the carrier and attached to the cam follower, the carrier having a slot therein constructed to permit passage through the carrier of the pump cam follower to the cam, the slot extending in a direction that falls in a plane through the axis of rotation, means for frictionally coupling the carrier to the cam to rotate with the cam, and means for limiting the rotation of the carrier but not the cam between two circumferential positions on the cam that correspond to at least two operative positions, to force the cam follower to move relative to the cam.

In accord with another aspect of the invention, there is provided, for the same dispensing mechanism as noted in the first sentence of the previous paragraph, an improvement wherein the cam includes a track surface extending vertically between a lowest position and positions above the lowest position and further including means for biasing the cam follower downward with a positive force when the cam follower is located at its lowest point of travel, so that a tip on the pump can be sealed by the positive force in a housing when it is in its downward, at least two operative positions.

Accordingly, it is an advantageous feature of the invention that a liquid-dispensing mechanism is provided that moves rotationally and vertically between at least two operational positions, using fewer and simpler parts than have heretofore been required to achieve the same motions for the same purpose.

Other advantageous features will become apparent upon reference to the following Description of the Preferred Embodiments when read in light of the attached drawings.

DESCRIPTION OF THE PREFERRED EMBODIMENTS

The invention is hereinafter described by reference to the preferred embodiments, in which the liquid to be aspirated and dispensed is a reference liquid used for potentiometric measurements, as shown with an analyzer of a particular construction. In addition, the invention is also useful to aspirate and dispense any other liquid, and regardless of the configuration of the rest of the analyzer.

Figure 1:
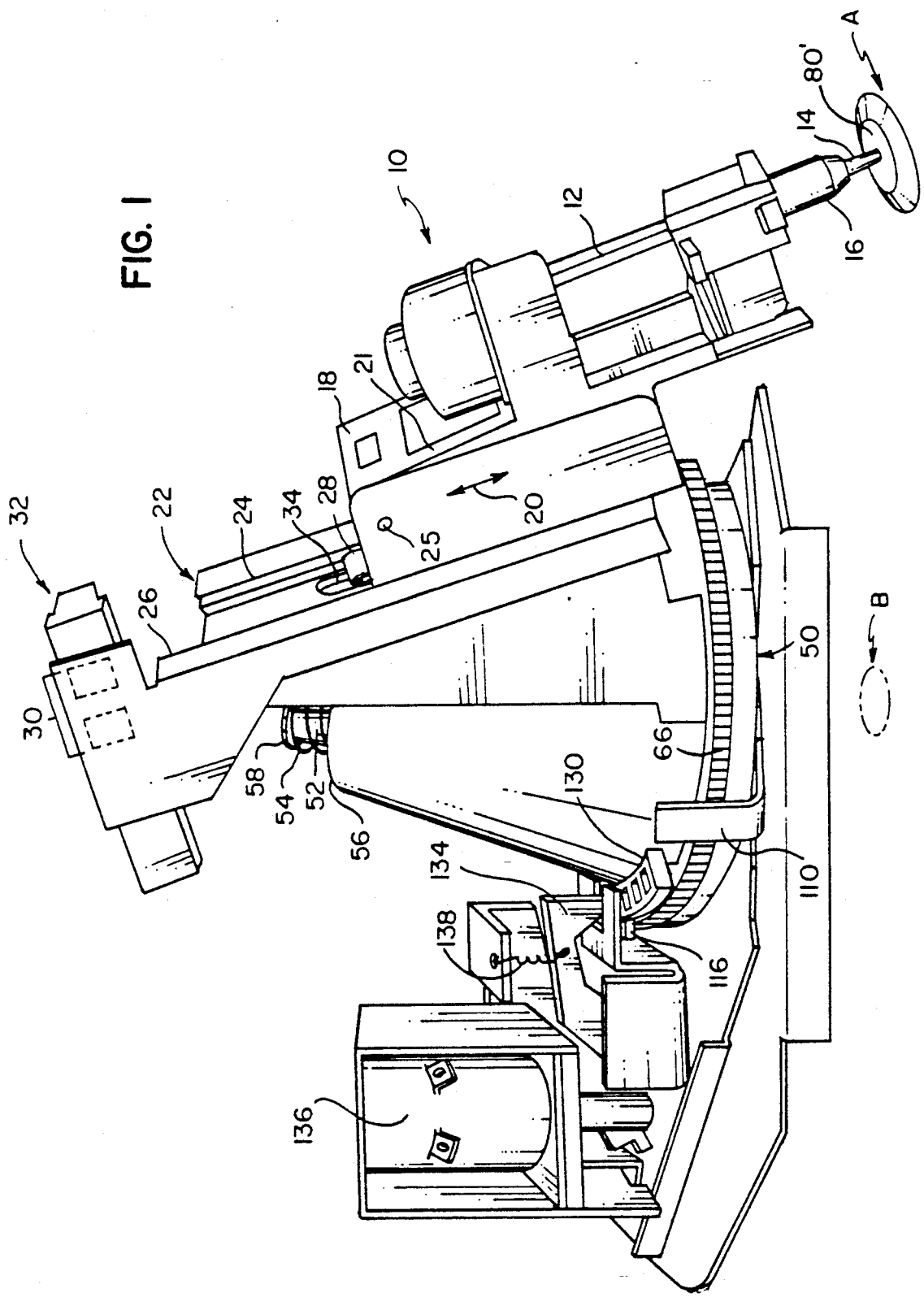
FIG. 1 is a perspective view of a liquid-aspirating and dispensing mechanism constructed in accordance with the invention.
Figure 2:
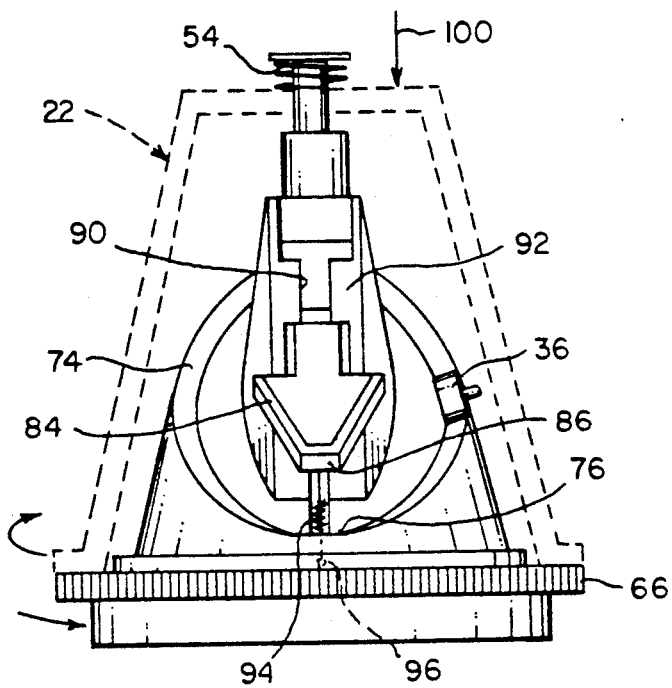
FIG. 2 is a fragmentary elevational view of the cam of the assembled mechanism of FIG. 1, showing the cam follower at a raised position at which the pump dispenser is inoperative, and the pump carrier in phantom.

A preferred liquid dispensing mechanism is shown in FIG. 1, to allow aspiration of liquid from station A, a reservoir of the liquid, and dispensing of a fraction or aliquot of the liquid so aspirated, at station B. These same stations are also shown, with more detail, in FIG. 8, described hereinafter. Alternatively, the positions of stations A & B can be reversed in some uses.

More specifically, the liquid dispensing mechanism 10 comprises a pump 12 of conventional construction similar to that used in the analyzer pump available on the analyzer from Eastman Kodak Company under the trademark "Ektachem 700", carrying a disposable tip 14 on a tip support 16. Pump 12 includes a housing 18 to which pump 12 is connected. Preferably, housing 18 of pump 12 comprises, FIG. 4, a body 19 that has a yoke 21 extending therefrom to two lugs 23 that pivot to frame 18 at 25. Housing 18 reciprocates, arrow 20, FIG. 1, on a carrier 22 having opposite rails 24,26 between which housing 18 slides. A position-sensor flag 28 is mounted on the top of housing 18 to cooperate with sensing means 30 located at the top 32 of carrier 22. See also FIG. 4.

Carrier 22, FIG. 1, is shaped to slip over a cam mechanism 50 that carrier 22 frictionally engages. A slot 34 is formed in carrier 22 between rails 24, 26 to allow a cam follower 36, FIG. 5, and its idler arm 38, to project through. Arm 38 is fixed to pump 12 or its housing 18. Preferably, a shoulder 40 projects from pump 12 or its housing to also guide the pump within slot 34.

Figure 5:
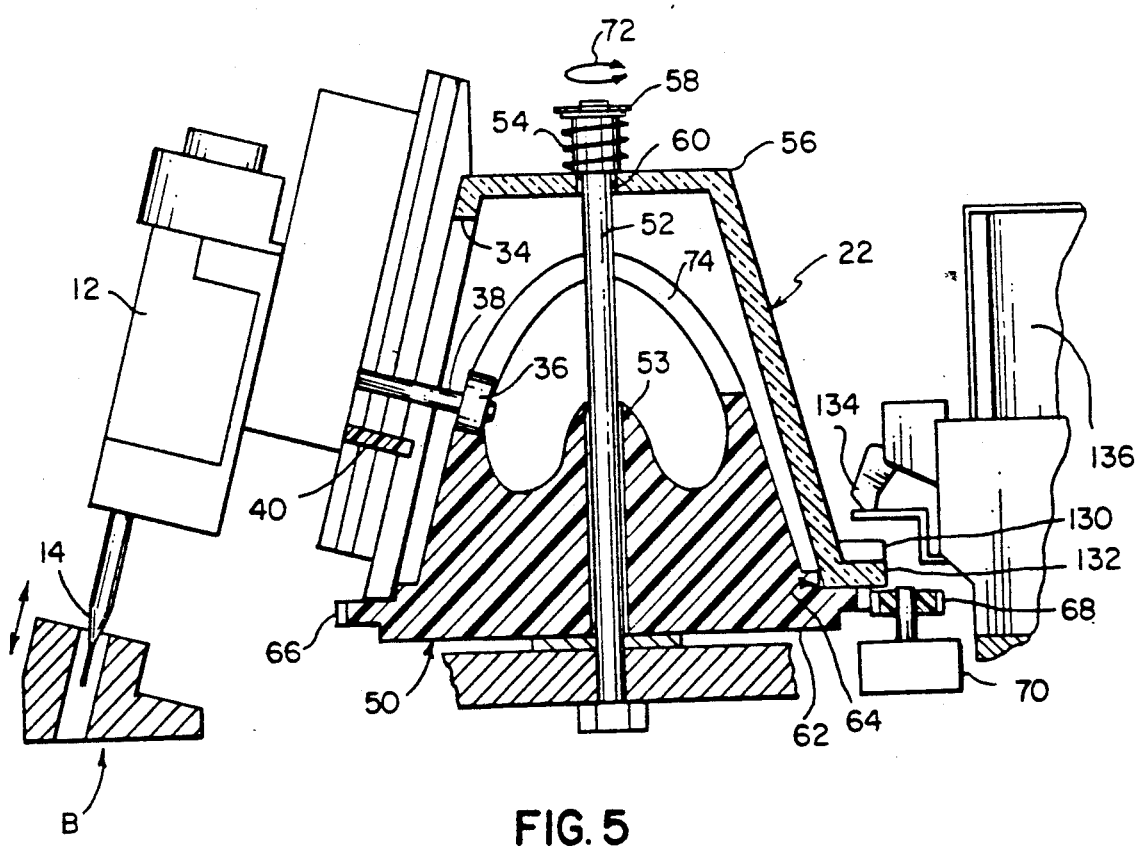
FIG. 5 is a section view taken generally along the line V—V of FIG. 3, to show the pump mounting on its carrier.

The frictional engagement of cam 50 by carrier 22 is preferably achieved, FIGS. 1 and 5, by a central fixed post 52 that passes through center portion 53 of the cam, FIG. 5, a compression spring 54 surrounding the post and bearing on end wall 56 of carrier 22, and a retaining clip 58. End wall 56 is apertured at 60, FIG. 5, to accommodate post 52 that projects therethrough.

Bottom wall 62 of cam 50 adjoins a curved sidewall 64 that is preferably provided with gear teeth 66. Most preferably, sidewall 64 at the teeth portion 66 is circular. Gear teeth 66 are positioned and shaped to engage a pinion gear 68 driven by a conventional motor 70, to cause cam 50 to rotate about the axis of post 52, arrow 72.

Figure 4:
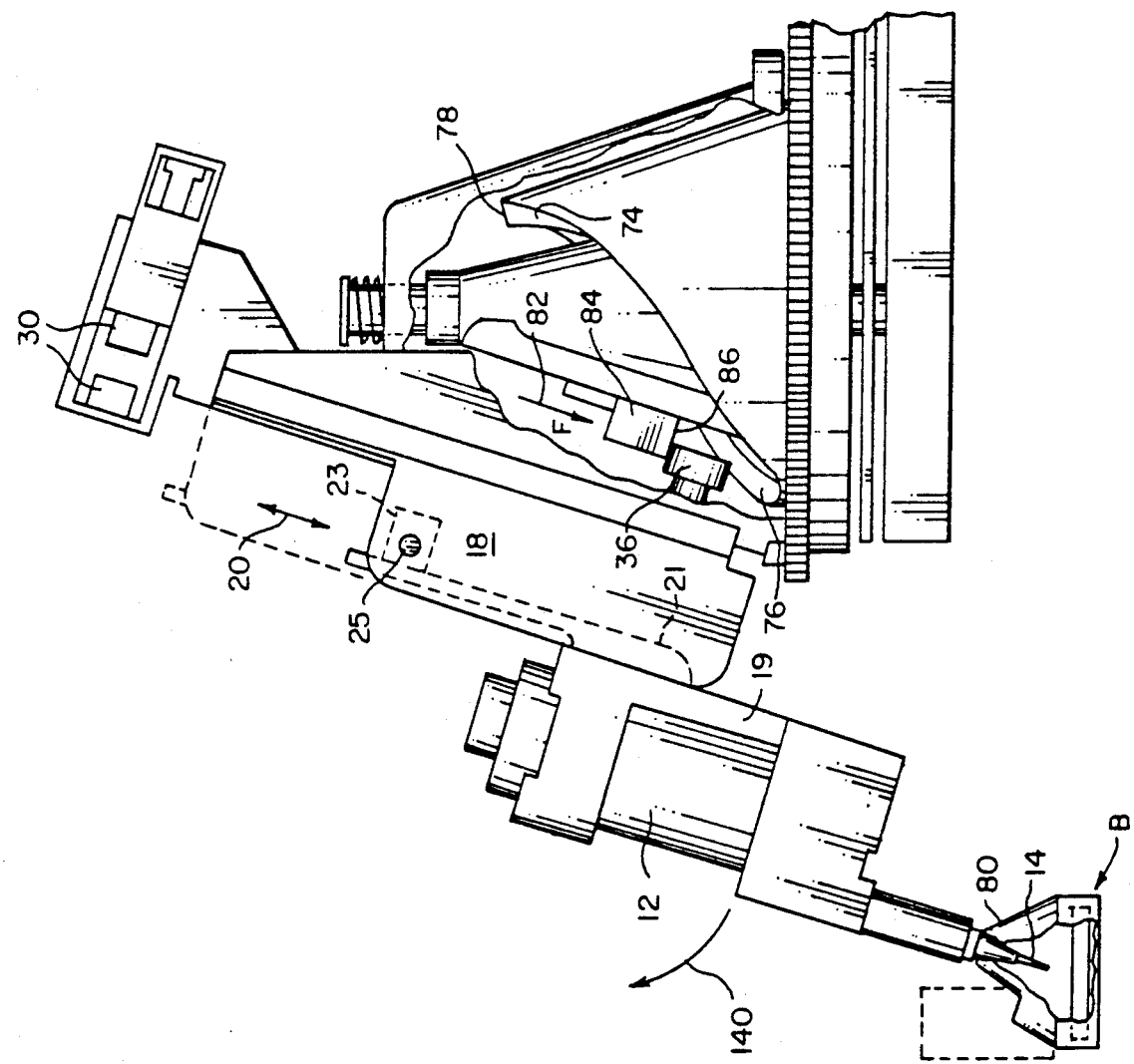
FIG. 4 is a partially broken away, elevational view but illustrating the cam follower in its lowermost position, wherein it is biased by the down-loading cam.
Figure 6A:
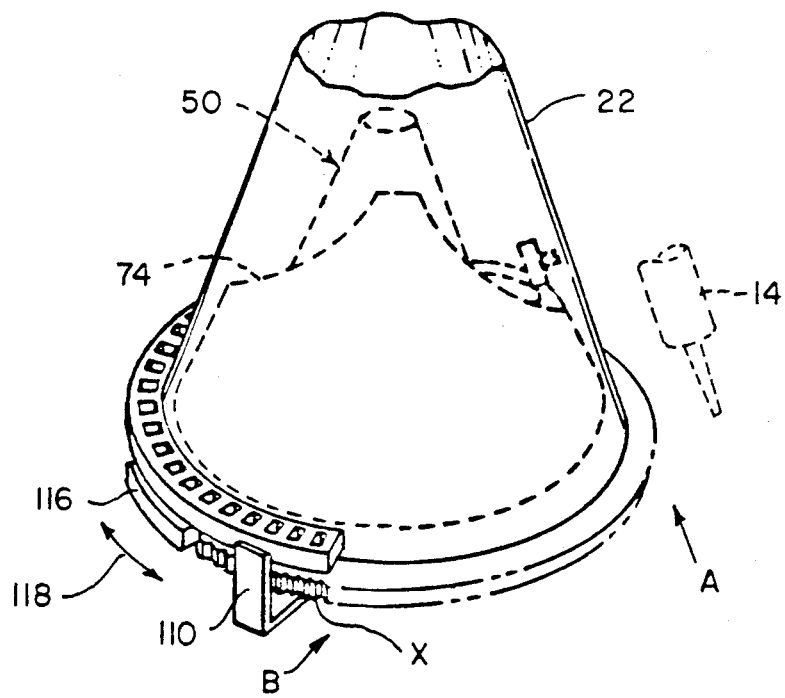
FIGS. 6A and 6B are fragmentary perspective views of the pump carrier and the cam (shown in phantom) to illustrate the relative movement between the two.
Figure 6B:
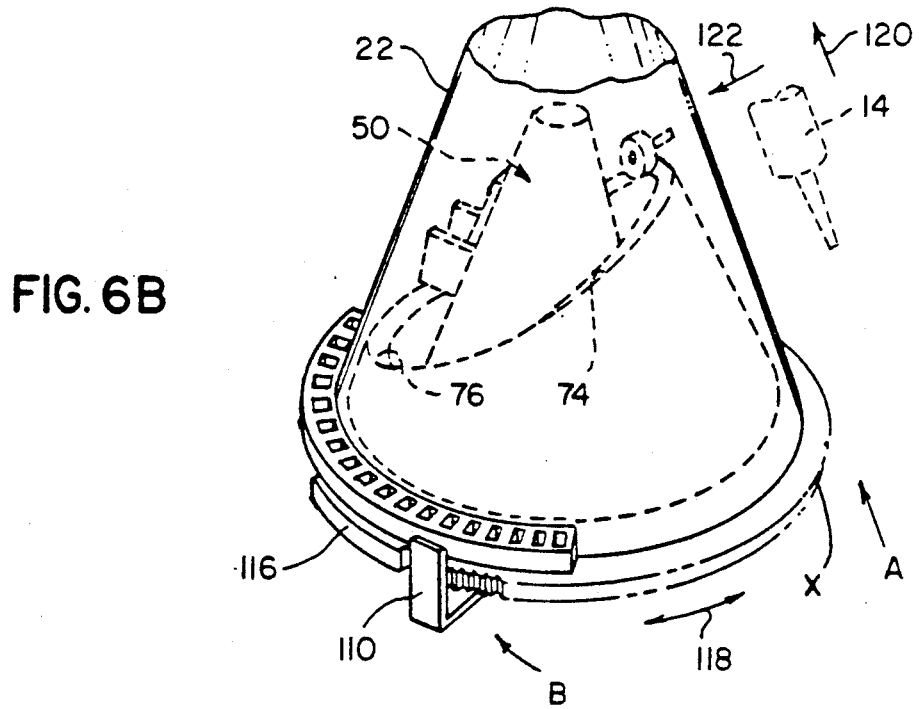

A critical aspect of cam 50 is cam track 74, extending in three dimensions around post 52, as shown in FIGS. 2, 4, 5 and 6A-6B. Track 74 includes a bottom-most portion 76, FIGS. 4 and 6B, and all the rest of the track that rises above that portion to completely encircle post 52, FIG. 5. Because cam 50 is preferably conical in overall shape as shown in this embodiment, track 74 also traces the surface of the cone defined by this portion of cam 50. The uppermost portion 78 of track 74 is generally opposite to the lowermost portion 76, that is, on the opposite side of post 52, as best shown in FIG. 4.

Cam follower 36 rides on track 74 due to gravity, except when pump carrier 22 and its cam follower are at bottom portion 76. At this time, the pump is at one of the two operative stations A or B, station B being schematically shown in FIG. 1 and partially schematically in FIG. 4. At either station, a top surface 80 or 80' is effective to resist further downward advance of tip 14 or pump 12. As a result, cam follower 36 is lifted off of track 74. However, to be sure that tip 14 is in fact completely seated at the station (for dispensing or aspirating, as the case may be), means are provided for biasing the cam follower downward with a predetermined positive force F, arrow 82, FIG. 4. Such means preferably comprise a downwardly-directed camming surface 84, preferably V-shaped with the bottom-most portion 86 representing the complete sealing position of cam follower 36, and hence of tip 14 at either station A or B. See especially FIG. 2.

To bias camming surface 84 downwardly, that surface is slidably mounted in a track 90 on face 92 of cam 50. Inside track 90, a tension spring 94 is connected at one end to surface 84, and at its opposite end 96 to cam 50.

Figure 3:
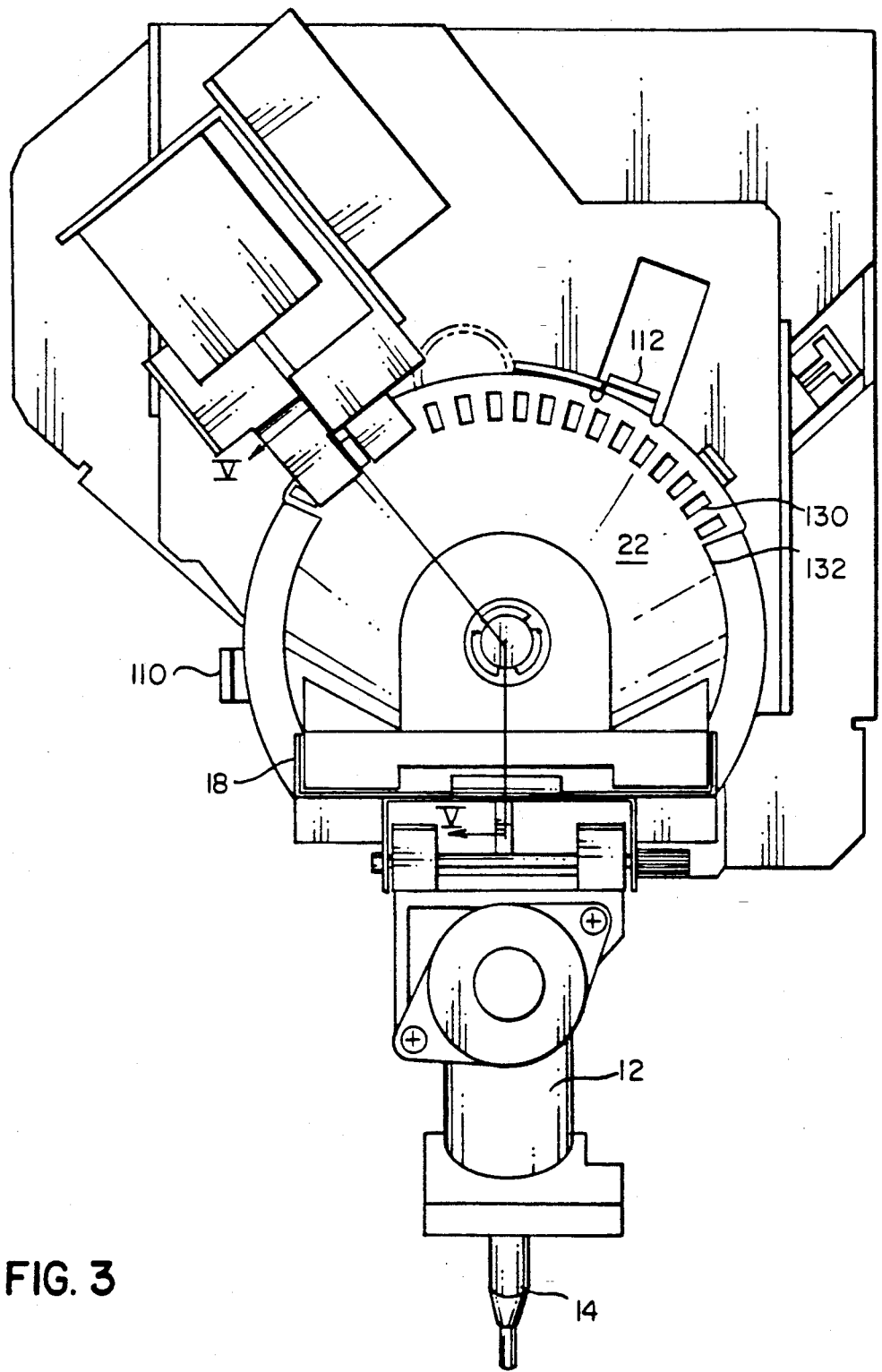
FIG. 3 is a plan view of the mechanism of FIG. 1.

Because of the downward force F, arrow 100 (FIG. 2), exerted by spring 54, pump carrier 22 generally rotates with cam 50 as it is driven to rotate. However, means are provided, such as two limit members 110 and 112 fixed to support 114 of mechanism 10, FIGS. 1 and 3, to stop rotation of carrier 22 and to confine its rotation within the arc between members 110 and 112. An outwardly projecting lip 116 is formed integral with carrier 22, FIG. 1 and especially FIGS. 6A and 6B. Lip 116 is sized and positioned to abut against either limit member 110 or 112 as cam 50 rotates, arrow 118, FIGS. 6A and 6B. The effect, of course, is to cause carrier 22 to come to a stop at a limit member, e.g., member 110, FIG. 6B, while cam 50 continues to rotate inside carrier 22. That is, gear tooth X, FIG. 6A, continues to rotate to its position shown in FIG. 6B, even though carrier 22 does not progress beyond the position shown in FIG. 6B. This in turn causes cam track 74 (in phantom) to continue to rotate relative to the now stationary carrier 22, as is shown by the relative positional changes of track 74 in FIG. 6B from that of FIG. 6A. Cam follower 36 in turn is forced, along with the pump and tip 14, to rise up since track 74 is "rising", arrow 120, FIG. 6B. In the raised "inoperative" position shown in FIG. 6B (in phantom), the pump and tip 14 are in position to be rotated (arrow 122) from that station (station A) to station B, without bumping into structure that is otherwise in the way. This is achieved by reversing the rotation of cam 50, arrow 124, at which time carrier 22 again moves with cam 50 until the other limit member (112, not shown in FIG. 6B) encounters lip 116 to force carrier 22 to once again stop while cam 50 continues in the direction of arrow 124.

Because the same reference liquid is aspirated from station A for many tests, tip 14 need not be replaced frequently. However, it is replaced for maintenance and cleanliness on occasion, e.g., every day, and for this purpose, means are included for removably locking carrier 22 to its last known position while tip 14 is manually removed. Such locking means preferably comprise, FIGS. 1 and 5, teeth 130 molded into side edge 132 of carrier 22, adjacent lip 116. Cooperating with teeth 130 is a lock lever 134 actuated by a solenoid 136 to be either in a raised position, as shown, or a lowered position to engage teeth 130 to lock against relative rotation of carrier 22. Optionally, a tension spring 138, FIG. 1, can be used to bias lever 134 upward into its disengaged position, so that solenoid 136 need only lower lever 134.

In use, lever 134 is effective to hold carrier 22 in place to allow maintenance of the pump and tip 14. For such maintenance, the pump 12 is preferably pivoted, arrow 140, upwardly about pivot 25, FIG. 4.

Figure 7:
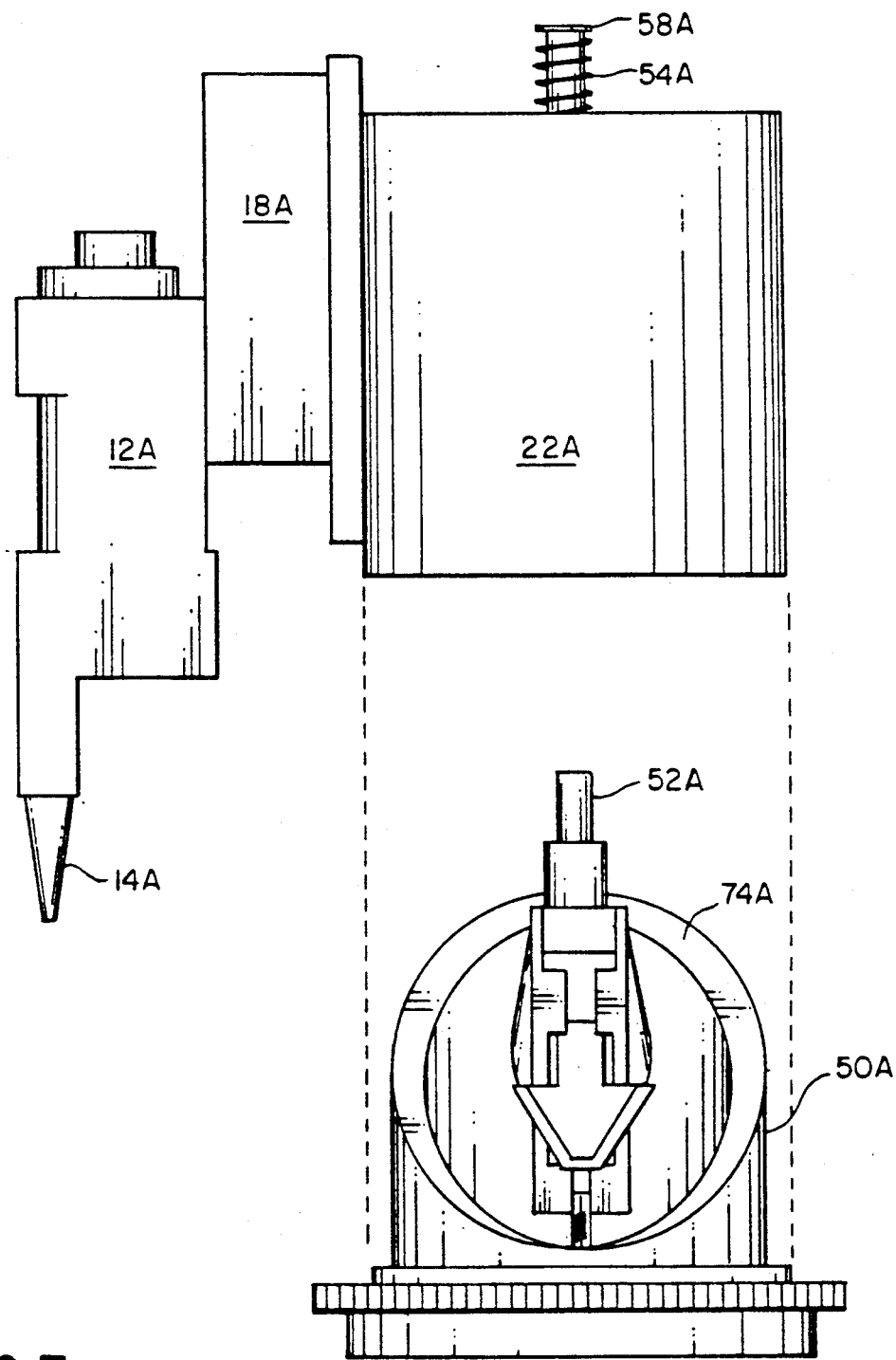
FIG. 7 is an exploded elevational view similar to that of FIG. 1, but illustrating an alternate embodiment of the invention.

Although the previous description is one of a conically shaped cam 50 and its carrier, to produce movement of tip 14 parallel to the tangent to the cone that has both a vertical and a horizontal component, other shapes are also useful. Thus, as shown in FIG. 7, the cam and the carrier can be cylindrical rather than conical. Parts similar to those previously described bear the same reference numeral, to which the distinguishing suffix "A" is appended. More specifically, pump 12A supports a tip 14A for reciprocation on carrier 22A that frictionally engages cam 50A by reason of compression spring 54A held by clip 58A, as before. The difference is, that the exterior shape of cam 50A is cylindrical, with track 74A being formed in the cylindrical wall of the cam, and carrier 22A is also cylindrical. As a result, the cam follower and resultant movement of pump 12A is only vertical or pivotal about post 52A, so that tip 14A lacks any horizontal component to its motion as dictated by cam 50A.

Figure 8:
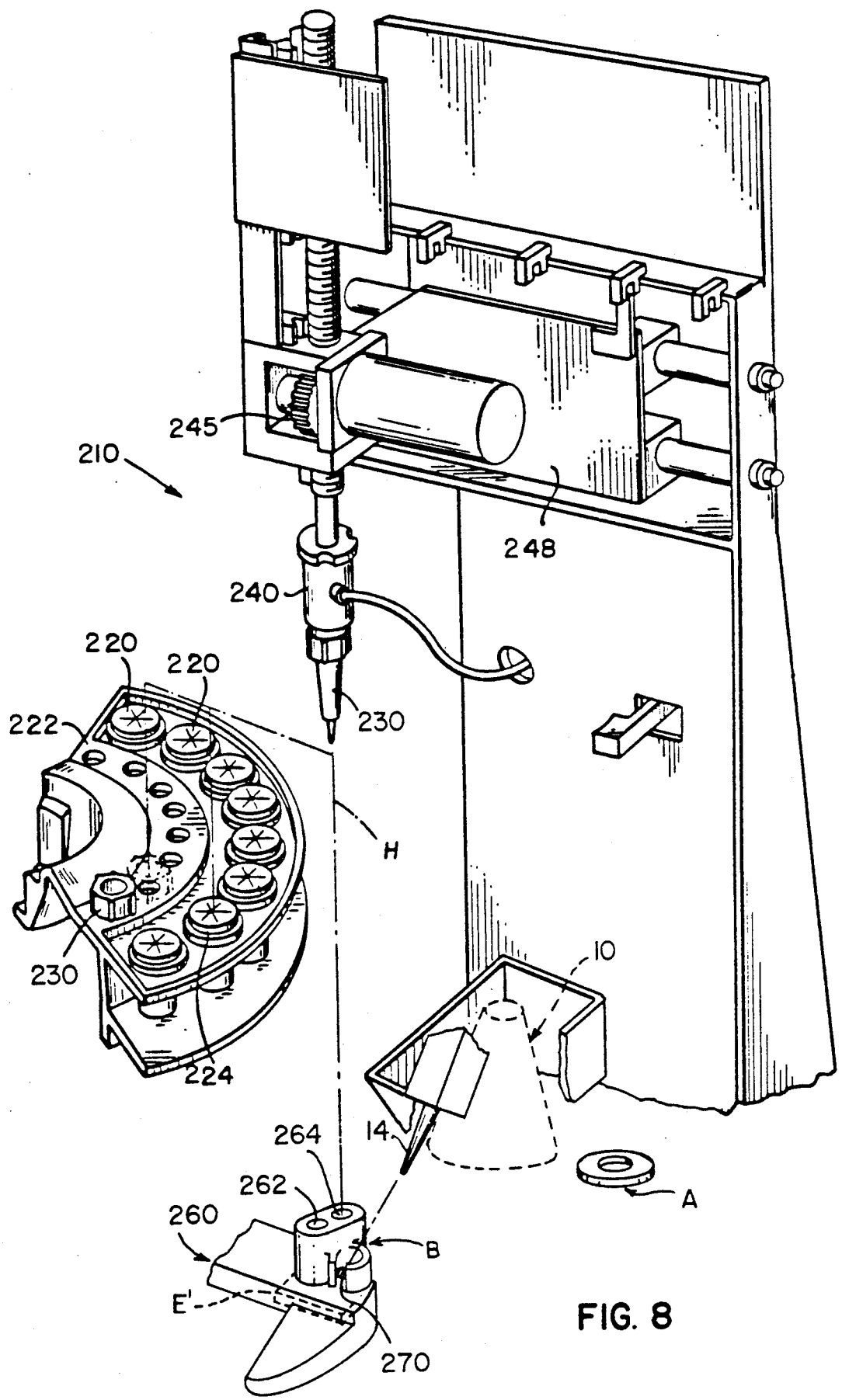
FIG. 8 is a perspective view illustrating the positioning of the mechanism of FIG. 1 in a clinical analyzer.

Either of the two dispensing mechanisms previously described can be used in any analyzer necessitating the dispensing of a reference liquid or some other standard liquid, such as a wash liquid. FIG. 8 illustrates the use of the mechanism of FIG. 1 in the analyzer available under the trademark "Ektachem 700" as noted above. More specifically, such an analyzer features a tray 222 containing cups of serum samples 220 and disposable tips 230, that cooperate with a dispensing station 210 having a pump 240. Station 210 is moved by cart 248 and gear 245 through the plane marked H to first pick up a tip, then penetrate caps 224 of cups 220 to aspirate sample, and then down into a slide block 260 and one of two entry ports 262, 264 on the block. (Slide block 260 is part of a rotating distributor arm, not shown.) A sloping side aperture 270 allows entry of tip 14 when slide block 260 is at station B as shown. Movement of tip 14 is of course dictated by mechanism 10 as it moves tip 14 from station A to station B. In this fashion, reference fluid is dispensed onto an ISE test element E' shown in phantom, while tip 230 dispenses a patient sample onto the same test element. After dispensing, tip 14 is preferably returned to station A where it is inserted to keep tip 14 from drying out.

In an alternative embodiment, not shown, a second pump housing and pump is mounted on the carrier circumferentially spaced from the first, to cooperate with the same dispensing station B. Such a second pump can be used to dispense a different liquid from the first. To stop the carrier in position to allow the second pump to move into station B, the lock lever (134 in FIG. 1) is actuated to engage the teeth on the carrier.

Figure 9:
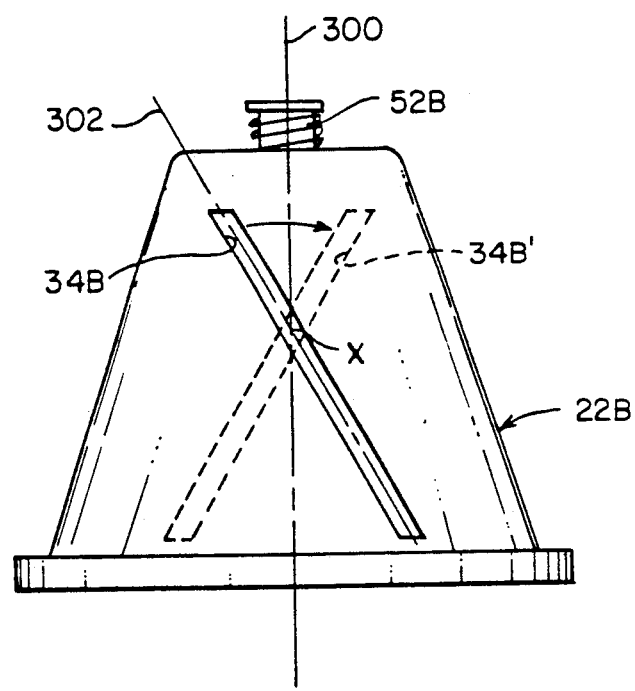
FIG. 9 is an elevational view of an alternate embodiment of the invention, wherein the carrier has been modified.

Slot 34, FIG. 5, of carrier 22 extends in a direction that is in a plane through the axis of rotation defined by post 52. That is, the slot and post are coplanar. Additionally, slot 34B can be non-coplanar with the axis of rotation 300, FIG. 9, as long as at least a portion of it falls in and defines a plane (which extends perpendicular to the sheet of the drawing, through line 302) that intersects the axis of rotation and post 52B at some point, e.g., point X. (Parts similar to those previously described bear the same reference numeral to which the distinguishing suffix "B" is attached.) As shown the entire slot lies in such a plane, since it is linear. Alternatively, the angling of slot 34B out of the plane of post 52B can be in either direction, as suggested by the alternate position 34B' shown in phantom. That is, the slot can be disposed anywhere between the position 34B and 34B'. The value of the angle out of the vertical is not critical, except that small angles, and particularly zero degrees, are preferred. The remainder of the mechanism, e.g. the cam, etc., is generally the same as described above.

The invention has been described in detail with particular reference to preferred embodiments thereof, but it will be understood that variations and modifications can be effected within the spirit and scope of the invention.

What is claimed is:

1. In a liquid dispensing mechanism for use in an analyzer and comprising a pump, a tip support on said pump for holding a liquid-containing tip, means for moving said pump and said tip support vertically and rotationally between at least two operative positions in which liquid is either aspirated into a tip or dispensed from a tip on said tip support, and inoperative positions above and between said operative positions, said moving means including a rotatable three-dimensional cam, a cam follower mounted to move on said cam, and means for rotating said cam about a vertical axis between said at least two operative positions in response to command signals, the improvement wherein said moving means further includes a carrier mounted over and surrounding said cam, said pump being slidably mounted for reciprocation on said carrier and attached to said cam follower, said carrier having a slot therein constructed to permit passage through said carrier of said pump cam follower to said cam, said slot extending in a direction that falls in a plane through said axis of rotation, means for frictionally coupling said carrier to said cam to rotate with said cam, and means for limiting the rotation of said carrier but not said cam between two circumferential positions on said cam that correspond to said at least two operative positions, to force said cam follower to move relative to said cam.

2. In a liquid dispensing mechanism for use in an analyzer and comprising a pump, a tip support on said pump for holding a liquid-containing tip, means for moving said pump and a tip on said support vertically and rotationally between at least two operative positions in which liquid is either aspirated into a tip or dispensed from a tip, and inoperative positions above and between said operative positions, said moving means including a rotatable three-dimensional cam, a cam follower mounted to move on said cam, and means for rotating said cam about a vertical axis between said at least two operative positions in response to command signals, the improvement wherein said moving means further includes a carrier mounted over and surrounding said cam, said pump being slidably mounted for reciprocation on said carrier and attached to said cam follower, said carrier having a slot therein constructed to permit passage through said carrier of said pump cam follower to said cam, at least a portion of said slot lying in and defining a plane that at least intersects said axis of rotation, means for frictionally coupling said carrier to said cam to rotate with said cam, and means for limiting the rotation of said carrier but not said cam between two circumferential positions on said cam that correspond to said at least two operative positions, to force said cam follower to move relative to said cam.

3. A mechanism as defined in claim 1 or 2, wherein said cam includes a downwardly extending track portion which extends below the lowest point of travel of which said pump cam follower is capable of traveling, and further including means for biasing said cam follower downward with a positive force when said cam follower is located at its lowest point of travel, so that a tip on said pump can be sealed by said positive force in a housing when it is in its downward, at least two operative positions.

4. A dispensing mechanism as defined in claim 1 or 2, and further including on said carrier, means for removably locking said carrier in any position between or at said at least two operative positions, so that maintenance can be performed on said pump without disturbing the last-known location of said carrier.

5. A dispensing mechanism as defined in claims 1, 3 or 4, wherein said cam is on the surface of a cylindrical barrel, and said carrier comprises a cylindrical housing that fits over said barrel.

6. A dispensing mechanism as defined in claims 1, 2, 3, or 4, wherein said cam is on a surface of a cone, and said carrier comprises a housing having a conical shape that fits over said cone.

7. In a liquid dispensing mechanism for use in an analyzer and comprising a pump, a tip support on said pump for holding a liquid-containing tip, means for moving said pump and tip support vertically and rotationally between at least two operative positions in which liquid is either aspirated into a tip or dispensed from a tip on said tip support, and inoperative positions above and between said operative positions, said moving means including a rotatable three-dimensional cam, a cam follower mounted to move on said cam, and means responsive to command signals for rotating said cam about a vertical axis between, and for stopping said carrier from rotating at, said at least two operative positions, the improvement wherein said moving means comprise a carrier on which said pump and said cam follower reciprocate, and means for mounting said carrier on said cam, and further including on said carrier, means for removably locking said carrier in any position between or at said at least two operative positions, so that maintenance can be performed on said pump without disturbing the last-known location of said carrier.

8. A dispensing mechanism as defined in claim 7, wherein said cam is on the surface of a cylindrical barrel, and said carrier comprises a cylindrical housing that fits over said barrel.

9. A dispensing mechanism as defined in claim 7, wherein said cam is on a surface of a cone, and said carrier comprises a housing having a conical shape that fits over said cone.

* * * * *